(12) United States Patent
Lee et al.

(10) Patent No.: US 11,259,567 B2
(45) Date of Patent: Mar. 1, 2022

(54) AEROSOL GENERATION DEVICE

(71) Applicant: KT&G CORPORATION, Daejeon (KR)

(72) Inventors: Jong Sub Lee, Seongnam-si (KR); In Seong Chun, Goyang-si (KR); Sung Rok Oh, Gunpo-si (KR)

(73) Assignee: KT&G CORPORATION, Daejeon (KR)

( * ) Notice: Subject to any disclaimer, the term of this patent is extended or adjusted under 35 U.S.C. 154(b) by 0 days.

(21) Appl. No.: 16/942,481

(22) Filed: Jul. 29, 2020

(65) Prior Publication Data

US 2020/0352235 A1      Nov. 12, 2020

Related U.S. Application Data

(63) Continuation of application No. 16/644,654, filed as application No. PCT/KR2018/006747 on Jun. 15, 2018.

(30) Foreign Application Priority Data

| Sep. 6, 2017 | (KR) | 10-2017-0113954 |
| Jun. 11, 2018 | (KR) | 10-2018-0067035 |

(51) Int. Cl.
| *A24F 40/40* | (2020.01) |
| *A24F 40/60* | (2020.01) |
| *A24F 40/20* | (2020.01) |

(52) U.S. Cl.
CPC .............. *A24F 40/40* (2020.01); *A24F 40/20* (2020.01); *A24F 40/60* (2020.01)

(58) Field of Classification Search
CPC ........ A24F 47/008; A24F 40/40; A24F 40/60; A24F 40/20
See application file for complete search history.

(56) References Cited

U.S. PATENT DOCUMENTS

| 2,638,904 A | 5/1956 | Mitchell |
| 4,637,407 A | 1/1987 | Bonanno et al. |
| (Continued) | | |

FOREIGN PATENT DOCUMENTS

| CA | 2 973 143 A1 | 8/2016 |
| CH | 310239 A | 12/1955 |
| (Continued) | | |

OTHER PUBLICATIONS

Office Action dated Feb. 7, 2020 from the Korean Intellectual Property Office in Application No. 10-2017-0146697.

(Continued)

*Primary Examiner* — Eric Yaary
*Assistant Examiner* — Jennifer A Kessie
(74) *Attorney, Agent, or Firm* — Sughrue Mion, PLLC

(57) ABSTRACT

An aerosol generation device may include a first housing comprising an opening at one side, an inner space for accommodating a cigarette inserted through the opening, and a heater disposed in the inner space; a second housing coupled to other side of the first housing and including a controller; a fastening portion configured to couple the first housing to the second housing; a battery coupled to the second housing; and a case coupled to the second housing for accommodating the second housing, the fastening portion, and the battery therein, wherein the fastening portion is prevented, by the case, from being exposed to outside.

7 Claims, 8 Drawing Sheets

(56) References Cited

U.S. PATENT DOCUMENTS

| | | |
|---|---|---|
| 5,144,962 A | 9/1992 | Counts et al. |
| 5,249,586 A | 1/1993 | Morgan et al. |
| 5,240,012 A | 8/1993 | Ehrman et al. |
| 5,388,594 A | 2/1995 | Counts et al. |
| 5,465,738 A | 11/1995 | Rowland |
| 5,479,948 A | 1/1996 | Counts et al. |
| 5,591,368 A | 1/1997 | Fleischhauer et al. |
| 5,666,977 A | 9/1997 | Higgins et al. |
| 5,878,752 A | 3/1999 | Adams et al. |
| 6,026,820 A | 2/2000 | Baggett, Jr. et al. |
| 6,053,176 A | 4/2000 | Adams et al. |
| 6,418,938 B1 | 7/2002 | Fleischhauer et al. |
| 6,532,965 B1 | 3/2003 | Abhulimen et al. |
| 6,615,840 B1 | 9/2003 | Fournier et al. |
| 6,810,883 B2 | 11/2004 | Fetter et al. |
| 7,861,726 B1 | 1/2011 | Lukasavitz |
| 8,375,959 B2 | 2/2013 | Dittrich et al. |
| 8,419,085 B2 | 4/2013 | Kim et al. |
| 8,752,545 B2 | 6/2014 | Buchberger |
| 8,851,081 B2 | 10/2014 | Fernando et al. |
| 8,973,587 B2 | 3/2015 | Liu |
| 9,078,472 B2 | 7/2015 | Liu |
| 9,078,473 B2 | 7/2015 | Worm et al. |
| 9,271,528 B2 | 3/2016 | Liu |
| 9,320,299 B2 | 4/2016 | Hearn et al. |
| 9,423,152 B2 | 8/2016 | Ampolini et al. |
| 9,427,023 B2 | 8/2016 | Liu |
| 9,497,991 B2 | 11/2016 | Besso et al. |
| 9,499,332 B2 | 11/2016 | Fernando et al. |
| 9,516,899 B2 | 12/2016 | Plojoux et al. |
| 9,560,883 B2 | 2/2017 | Hawes |
| 9,655,383 B2 | 5/2017 | Holzherr et al. |
| 9,693,587 B2 | 7/2017 | Plojoux et al. |
| 9,723,871 B2 | 8/2017 | Xiang |
| 9,814,263 B2 | 11/2017 | Cochand et al. |
| 9,854,841 B2 | 1/2018 | Ampolini et al. |
| 9,894,934 B2 | 2/2018 | Li et al. |
| 9,918,494 B2 | 3/2018 | Mironov |
| 9,955,724 B2 | 5/2018 | Lord |
| 9,986,760 B2 | 6/2018 | Macko et al. |
| 9,999,247 B2 | 6/2018 | Ruscio et al. |
| 10,015,990 B2 | 7/2018 | Mironov |
| 10,031,183 B2 | 7/2018 | Novak, III et al. |
| 10,070,667 B2 | 9/2018 | Lord et al. |
| 10,104,911 B2 | 10/2018 | Thorens et al. |
| 10,130,780 B2 | 11/2018 | Talon |
| 10,136,673 B2 | 11/2018 | Mironov |
| 10,159,283 B2 | 12/2018 | Mironov |
| 10,194,697 B2 | 2/2019 | Fernando et al. |
| 10,299,513 B2 | 5/2019 | Perez et al. |
| 10,368,584 B2 | 8/2019 | Fernando et al. |
| 10,439,419 B2 | 10/2019 | Bernauer et al. |
| 10,440,987 B2 | 10/2019 | Zeng et al. |
| 10,448,670 B2 | 10/2019 | Talon et al. |
| 10,492,542 B1 | 12/2019 | Worm et al. |
| 10,548,350 B2 | 2/2020 | Griem et al. |
| 10,555,553 B2 | 2/2020 | Binassi et al. |
| 10,587,737 B2 | 3/2020 | Yoo et al. |
| 10,588,351 B2 | 3/2020 | Ricketts |
| 10,645,971 B2 | 5/2020 | Zitzke |
| 10,667,329 B2 | 5/2020 | Bernauer et al. |
| 10,668,058 B2 | 6/2020 | Rose et al. |
| 10,716,329 B2 | 7/2020 | Matsumoto et al. |
| 10,813,174 B2 | 10/2020 | Schneider et al. |
| 10,869,499 B2 | 12/2020 | Fernando et al. |
| 10,869,503 B2 | 12/2020 | Yamada et al. |
| 10,881,131 B2 | 1/2021 | Matsumoto et al. |
| 10,881,137 B2 | 1/2021 | Suzuki et al. |
| 10,881,143 B2 | 1/2021 | Suzuki et al. |
| 11,039,642 B2 | 6/2021 | Zuber et al. |
| 11,147,316 B2 | 10/2021 | Farine et al. |
| 2004/0261802 A1 | 12/2004 | Griffin et al. |
| 2005/0045198 A1 | 3/2005 | Larson et al. |
| 2005/0172976 A1 | 8/2005 | Newman et al. |
| 2008/0001052 A1 | 1/2008 | Kalous et al. |
| 2010/0307518 A1 | 12/2010 | Wang |
| 2011/0155151 A1 | 6/2011 | Newman et al. |
| 2011/0290248 A1 | 12/2011 | Schennum |
| 2011/0290269 A1 | 12/2011 | Shimizu |
| 2012/0247494 A1 | 10/2012 | Oglesby et al. |
| 2013/0037041 A1 | 2/2013 | Worm et al. |
| 2013/0213419 A1 | 8/2013 | Tucker et al. |
| 2013/0284192 A1 | 10/2013 | Peleg et al. |
| 2013/0340775 A1 | 12/2013 | Juster et al. |
| 2014/0020698 A1 | 1/2014 | Fiebelkorn |
| 2014/0096782 A1 | 4/2014 | Ampolini et al. |
| 2014/0116455 A1 | 5/2014 | Youn |
| 2014/0246035 A1 | 9/2014 | Minskoff et al. |
| 2014/0299137 A1 | 10/2014 | Kieckbusch et al. |
| 2014/0301721 A1 | 10/2014 | Ruscio et al. |
| 2014/0305448 A1 | 10/2014 | Zuber et al. |
| 2014/0318559 A1 | 10/2014 | Thorens et al. |
| 2014/0345634 A1 | 11/2014 | Zuber et al. |
| 2014/0363145 A1 | 12/2014 | Plojoux et al. |
| 2015/0007838 A1 | 1/2015 | Fernando et al. |
| 2015/0013696 A1 | 1/2015 | Plojoux et al. |
| 2015/0020832 A1 | 1/2015 | Greim et al. |
| 2015/0024355 A1 | 1/2015 | Ghofrani et al. |
| 2015/0027474 A1 | 1/2015 | Zuber et al. |
| 2015/0100441 A1 | 4/2015 | Alarcon et al. |
| 2015/0136124 A1 | 5/2015 | Aronie et al. |
| 2015/0136154 A1 | 5/2015 | Mitrev et al. |
| 2015/0208725 A1 | 7/2015 | Tsai |
| 2015/0245654 A1 | 9/2015 | Memari et al. |
| 2015/0257445 A1 | 9/2015 | Henry, Jr. et al. |
| 2015/0272211 A1 | 10/2015 | Chung |
| 2016/0150824 A1 | 6/2016 | Memari et al. |
| 2016/0270437 A1 | 9/2016 | Nappi |
| 2016/0270449 A1 | 9/2016 | Hon |
| 2016/0286861 A1 | 10/2016 | Liu |
| 2016/0302488 A1 | 10/2016 | Fernando et al. |
| 2016/0331032 A1 | 11/2016 | Malgat et al. |
| 2016/0345629 A1 | 12/2016 | Mironov |
| 2016/0366946 A1 | 12/2016 | Murison et al. |
| 2017/0006916 A1 | 1/2017 | Liu |
| 2017/0027229 A1 | 2/2017 | Cameron |
| 2017/0027234 A1 | 2/2017 | Farine et al. |
| 2017/0042243 A1 | 2/2017 | Plojoux et al. |
| 2017/0055580 A1 | 3/2017 | Blandino et al. |
| 2017/0071251 A1 | 3/2017 | Goch |
| 2017/0095006 A1 | 4/2017 | Egoyants et al. |
| 2017/0150757 A1 | 6/2017 | Worm et al. |
| 2017/0164659 A1 | 6/2017 | Schneider et al. |
| 2017/0172214 A1 | 6/2017 | Li et al. |
| 2017/0172215 A1 | 6/2017 | Li et al. |
| 2017/0188634 A1 | 7/2017 | Plojoux et al. |
| 2018/0177234 A1 | 6/2018 | Lee |
| 2018/0206556 A1 | 7/2018 | Thorens et al. |
| 2018/0235283 A1 | 8/2018 | Zuber et al. |
| 2019/0014826 A1 | 1/2019 | Thorens et al. |
| 2019/0320719 A1 | 10/2019 | Liu et al. |
| 2019/0364975 A1 | 12/2019 | Fernando et al. |
| 2020/0006950 A1 | 1/2020 | Holzherr |
| 2020/0120983 A1 | 4/2020 | Chen |
| 2020/0221778 A1* | 7/2020 | Trzecieski ............ A24F 40/10 |
| 2020/0232766 A1 | 7/2020 | Flick |
| 2020/0305508 A1 | 10/2020 | Talon |
| 2020/0352224 A1 | 11/2020 | Plojoux et al. |
| 2020/0413495 A1 | 12/2020 | Schneider et al. |
| 2021/0000182 A1 | 1/2021 | Ruscio et al. |
| 2021/0120875 A1 | 4/2021 | Mironov |

FOREIGN PATENT DOCUMENTS

| | | |
|---|---|---|
| CN | 1102964 A | 5/1995 |
| CN | 1209731 A | 3/1999 |
| CN | 1973706 A | 6/2007 |
| CN | 101043827 A | 9/2007 |
| CN | 101444335 A | 6/2009 |
| CN | 102006790 A | 4/2011 |
| CN | 102438470 A | 5/2012 |
| CN | 202407082 U | 9/2012 |
| CN | 202774134 U | 3/2013 |
| CN | 103096741 A | 5/2013 |

(56) References Cited

FOREIGN PATENT DOCUMENTS

| | | |
|---|---|---|
| CN | 103281920 A | 9/2013 |
| CN | 103338665 A | 10/2013 |
| CN | 203457802 U | 3/2014 |
| CN | 103859606 A | 6/2014 |
| CN | 203633505 U | 6/2014 |
| CN | 103929988 A | 7/2014 |
| CN | 203689071 U | 7/2014 |
| CN | 103974640 A | 8/2014 |
| CN | 103997921 A | 8/2014 |
| CN | 103997922 A | 8/2014 |
| CN | 203789137 U | 8/2014 |
| CN | 104023568 A | 9/2014 |
| CN | 104023574 A | 9/2014 |
| CN | 104039183 A | 9/2014 |
| CN | 104095295 A | 10/2014 |
| CN | 104106842 A | 10/2014 |
| CN | 203943078 U | 11/2014 |
| CN | 204070570 U | 1/2015 |
| CN | 204146338 U | 2/2015 |
| CN | 104382237 A | 3/2015 |
| CN | 104470387 A | 3/2015 |
| CN | 104489933 A | 4/2015 |
| CN | 104544559 A | 4/2015 |
| CN | 204317504 U | 5/2015 |
| CN | 104754964 A | 7/2015 |
| CN | 104770878 A | 7/2015 |
| CN | 104812260 A | 7/2015 |
| CN | 204444239 U | 7/2015 |
| CN | 204763414 U | 11/2015 |
| CN | 105163610 A | 12/2015 |
| CN | 105208882 A | 12/2015 |
| CN | 105208884 A | 12/2015 |
| CN | 105341993 A | 2/2016 |
| CN | 105342011 A | 2/2016 |
| CN | 105357994 A | 2/2016 |
| CN | 205018293 U | 2/2016 |
| CN | 105361250 A | 3/2016 |
| CN | 105453598 A | 3/2016 |
| CN | 205180371 U | 4/2016 |
| CN | 205197003 U | 5/2016 |
| CN | 205337598 U | 6/2016 |
| CN | 205337598 U | 6/2016 |
| CN | 105747281 A | 7/2016 |
| CN | 10587869 A | 8/2016 |
| CN | 105831812 A | 8/2016 |
| CN | 205512358 U | 8/2016 |
| CN | 205597118 U | 9/2016 |
| CN | 106037014 A | 10/2016 |
| CN | 205648910 U | 10/2016 |
| CN | 106102492 A | 11/2016 |
| CN | 106132217 A | 11/2016 |
| CN | 106163307 A | 11/2016 |
| CN | 205728067 U | 11/2016 |
| CN | 106174699 A | 12/2016 |
| CN | 106231934 A | 12/2016 |
| CN | 106413439 A | 2/2017 |
| CN | 106413444 A | 2/2017 |
| CN | 106455708 A | 2/2017 |
| CN | 106455714 A | 2/2017 |
| CN | 106455716 A | 2/2017 |
| CN | 106473233 A | 3/2017 |
| CN | 106901404 A | 6/2017 |
| DE | 3302518 A1 | 7/1984 |
| EA | 12169 B1 | 10/2007 |
| EA | 026076 B1 | 2/2017 |
| EP | 1119267 B1 | 7/2004 |
| EP | 2 201 850 A1 | 6/2010 |
| EP | 2253233 A1 | 11/2010 |
| EP | 2 471 392 B1 | 9/2013 |
| EP | 2 531 053 B1 | 9/2015 |
| EP | 3 098 738 A1 | 11/2016 |
| EP | 2 432 339 B1 | 3/2017 |
| EP | 3 179 828 A1 | 6/2017 |
| EP | 3 248 485 B1 | 4/2020 |
| EP | 3 275 319 B1 | 8/2020 |
| GB | 2542018 A | 3/2017 |
| JP | 3-232481 A | 10/1991 |
| JP | 7-184627 A | 7/1995 |
| JP | 11-164679 A | 6/1999 |
| JP | 3645921 B2 | 2/2005 |
| JP | 2006-320286 A | 11/2006 |
| JP | 4278306 B2 | 6/2009 |
| JP | 2010-178730 A | 8/2010 |
| JP | 2010-526553 A | 8/2010 |
| JP | 2011-87569 A | 5/2011 |
| JP | 2011-518567 A | 6/2011 |
| JP | 4739433 B2 | 8/2011 |
| JP | 2012-527222 A | 11/2012 |
| JP | 2014-500017 A | 1/2014 |
| JP | 2014-521419 A | 8/2014 |
| JP | 2014-525237 A | 9/2014 |
| JP | 2014-533513 A | 12/2014 |
| JP | 2014-534813 A | 12/2014 |
| JP | 2015-503916 A | 2/2015 |
| JP | 2015-506170 A | 3/2015 |
| JP | 2015-507477 A | 3/2015 |
| JP | 2015-508996 A | 3/2015 |
| JP | 2015-524261 A | 8/2015 |
| JP | 2015-180214 A | 10/2015 |
| JP | 2015-529458 A | 10/2015 |
| JP | 2015-204833 A | 11/2015 |
| JP | 2016-528910 A | 9/2016 |
| JP | 2017-51189 A | 3/2017 |
| JP | 2017-70297 A | 4/2017 |
| JP | 2017-514463 A | 6/2017 |
| KR | 10-0304044 A | 11/2001 |
| KR | 10-0806461 B1 | 2/2008 |
| KR | 10-0965099 B1 | 6/2010 |
| KR | 10-1001077 B1 | 12/2010 |
| KR | 10-2011-0096548 A | 8/2011 |
| KR | 20-2011-0009632 U | 10/2011 |
| KR | 10-1098112 B1 | 12/2011 |
| KR | 10-2012-0027029 A | 3/2012 |
| KR | 10-2012-0101637 A | 9/2012 |
| KR | 10-1184499 B1 | 9/2012 |
| KR | 10-2012-0109634 A | 10/2012 |
| KR | 10-2012-0114333 A | 10/2012 |
| KR | 10-2012-0121314 A | 11/2012 |
| KR | 10-2013-0027909 A | 3/2013 |
| KR | 20-0466757 Y1 | 5/2013 |
| KR | 10-2013-0081238 A | 7/2013 |
| KR | 10-2013-0139296 A | 12/2013 |
| KR | 10-2014-0068203 A | 6/2014 |
| KR | 10-2014-0092312 A1 | 7/2014 |
| KR | 10-2014-0109455 A | 9/2014 |
| KR | 10-2014-0116055 A | 10/2014 |
| KR | 10-2014-0118983 A | 10/2014 |
| KR | 10-2014-0119072 A | 10/2014 |
| KR | 10-2014-0135774 A | 11/2014 |
| KR | 10-2015-0030409 A | 3/2015 |
| KR | 10-2015-0033617 A | 4/2015 |
| KR | 10-2015-0058569 A | 5/2015 |
| KR | 10-1516304 B1 | 5/2015 |
| KR | 10-1523088 B1 | 5/2015 |
| KR | 10-2015-0099771 A | 9/2015 |
| KR | 10-2016-0009678 A | 1/2016 |
| KR | 10-2016-0012110 A | 2/2016 |
| KR | 10-2016-0012329 A | 2/2016 |
| KR | 10-2016-0015144 A | 2/2016 |
| KR | 10-2016-0040643 A | 4/2016 |
| KR | 10-1609715 B1 | 4/2016 |
| KR | 10-1614171 B1 | 4/2016 |
| KR | 10-2016-0052607 A | 5/2016 |
| KR | 10-1619032 B1 | 5/2016 |
| KR | 20-2016-0001476 U | 5/2016 |
| KR | 10-2016-0060006 A | 6/2016 |
| KR | 10-2016-0088163 A | 7/2016 |
| KR | 10-2016-0094938 A | 8/2016 |
| KR | 10-2016-0096744 A | 8/2016 |
| KR | 10-2016-0108855 A | 9/2016 |
| KR | 10-1656061 | 9/2016 |
| KR | 10-2016-0114743 A | 10/2016 |
| KR | 10-2016-0124091 A | 10/2016 |
| KR | 10-1667124 B1 | 10/2016 |

(56) References Cited

FOREIGN PATENT DOCUMENTS

| | | |
|---|---|---|
| KR | 10-1668175 B1 | 10/2016 |
| KR | 10-2016-0129024 A | 11/2016 |
| KR | 10-2016-0131035 A | 11/2016 |
| KR | 10-2016-0133665 A | 11/2016 |
| KR | 10-2016-0137627 A | 11/2016 |
| KR | 10-1679489 B1 | 11/2016 |
| KR | 10-2016-0140608 A | 12/2016 |
| KR | 10-2016-0142896 A | 12/2016 |
| KR | 10-2016-0147253 A | 12/2016 |
| KR | 10-1690389 B1 | 12/2016 |
| KR | 10-2017-0006282 A | 1/2017 |
| KR | 10-2017-0007262 A | 1/2017 |
| KR | 10-2017-0044158 A | 4/2017 |
| KR | 10-1740160 | 5/2017 |
| KR | 10-2017-0071486 A | 6/2017 |
| KR | 10-2017-0074898 A | 6/2017 |
| KR | 1020180020705 A | 2/2018 |
| RU | 2302806 C2 | 7/2007 |
| RU | 2425608 C2 | 8/2011 |
| RU | 2 531 890 C2 | 10/2014 |
| RU | 2564600 C1 | 10/2015 |
| RU | 2014 125 232 A | 12/2015 |
| RU | 2581999 C2 | 4/2016 |
| RU | 2589437 C2 | 7/2016 |
| RU | 2594557 C2 | 8/2016 |
| RU | 2595593 C2 | 8/2016 |
| RU | 2 602 053 C2 | 11/2016 |
| RU | 2 602 962 C2 | 11/2016 |
| RU | 2 603 559 C2 | 11/2016 |
| RU | 2 604 012 C2 | 12/2016 |
| RU | 2604012 C2 | 12/2016 |
| WO | 9406314 A1 | 3/1994 |
| WO | 98/23171 A1 | 6/1998 |
| WO | 00/27232 A1 | 5/2000 |
| WO | 2010/133342 A1 | 11/2010 |
| WO | 2011/028372 A1 | 3/2011 |
| WO | 2011/095781 A1 | 8/2011 |
| WO | 2012/072264 A1 | 6/2012 |
| WO | 2012/123702 A1 | 9/2012 |
| WO | 2013/034458 A1 | 3/2013 |
| WO | 2013/060743 A2 | 5/2013 |
| WO | 2013/076098 A2 | 5/2013 |
| WO | 2013/098395 A1 | 7/2013 |
| WO | 2013/098398 A3 | 7/2013 |
| WO | 2013/098409 A1 | 7/2013 |
| WO | 2013/102609 A2 | 7/2013 |
| WO | 2013/102612 A2 | 7/2013 |
| WO | 2013102609 A2 | 7/2013 |
| WO | 2013/120565 A3 | 8/2013 |
| WO | 2013/126777 A2 | 8/2013 |
| WO | 2013/137084 A1 | 9/2013 |
| WO | 2013/171217 A1 | 11/2013 |
| WO | 2014/029880 A2 | 2/2014 |
| WO | 2015/046386 A1 | 4/2015 |
| WO | 2015/088744 A1 | 6/2015 |
| WO | 2015/128665 A1 | 9/2015 |
| WO | 2015/155289 A1 | 10/2015 |
| WO | 2015/165813 A1 | 11/2015 |
| WO | 2015/177044 A1 | 11/2015 |
| WO | 2015/197627 A1 | 12/2015 |
| WO | 2016/059073 A1 | 4/2016 |
| WO | 2016/075028 A1 | 5/2016 |
| WO | 2016/076147 A1 | 5/2016 |
| WO | 2016/107766 A1 | 7/2016 |
| WO | 2016/124550 A1 | 8/2016 |
| WO | 2016/124552 A1 | 8/2016 |
| WO | 2016/150019 A1 | 9/2016 |
| WO | 2016/156103 A1 | 10/2016 |
| WO | 2016/156219 A1 | 10/2016 |
| WO | 2016/159013 A1 | 10/2016 |
| WO | 2016166064 A1 | 10/2016 |
| WO | 2016178377 A1 | 11/2016 |
| WO | 2017/029088 A1 | 2/2017 |
| WO | 2017/029089 A1 | 2/2017 |
| WO | 2017/037457 A1 | 3/2017 |
| WO | 2017/042297 A1 | 3/2017 |
| WO | 2017/075759 A1 | 5/2017 |
| WO | 2017/139963 A1 | 8/2017 |
| WO | 2018050449 A1 | 3/2018 |
| WO | 2018/189195 A1 | 10/2018 |
| WO | 2019/020826 A1 | 1/2019 |
| WO | 2019/030172 A1 | 2/2019 |
| WO | 2019/095268 A1 | 5/2019 |

OTHER PUBLICATIONS

International Search Report dated May 29, 2018 in PCT/KR2017/012486.
Office Action dated Jun. 27, 2019, from the Korean Intellectual Property Office in Application No. 10-2018-0063759.
International Search Report dated Nov. 30, 2018 in PCT/KR2018/006702.
Office Action dated Aug. 7, 2019, from the Korean Intellectual Property Office in Application No. 10-2018-0067035.
International Search Report dated Aug. 29, 2018 in PCT/KR2018/005945.
International Search Report dated Dec. 4, 2018 in PCT/KR2018/006747.
Office Action dated Jun. 19, 2019, from the Korean Intellectual Property Office in Application No. 10-2018-0059279.
Notice of Allowance dated Jul. 17, 2019 in the Korean Patent Office in corresponding Korean Application No. 10-2019-0027638.
Partial supplementary European search report dated Aug. 3, 2020 in Application No. 17880867.1.
Extended European search report dated Nov. 4, 2020 by the European Patent Office in Application No. 17880867.1.
Office Action dated Oct. 29, 2020 by the Korean Patent Office in Application No. 10-2018-0010837.
Office Action dated Nov. 4, 2020 by the Japanese Patent Office in Application No. 2019-554453.
Office Action dated Nov. 4, 2020 by the Japanese Patent Office in Application No. 2020-128346.
Decision on Grant dated Nov. 26, 2020 by the Russian Federal Service For Intellectual Property Patent Application No. 2020124607.
Office Action dated Nov. 26, 2020 by Russian Federal Service For Intellectual Property Office Patent Application No. 2020124609.
Decision on Grant dated Oct. 26, 2020 by Russian Federal Service For Intellectual Property in Application No. 2020124610.
Office Action dated Jun. 29, 2020 by the Korean Patent Office in Application No. 10-2018-0010836.
Extended European Search Report dated Dec. 11, 2020 in European Application No. 20188967.2.
Extended European Search Report dated Jan. 15, 2021 in European Application No. 20188949.0.
Extended European Search Report dated Dec. 16, 2020 in European Application No. 20188985.4.
Office Action dated Dec. 30, 2020 in Russian Application No. 2020124651.
Office Action dated Dec. 28, 2020 in Russian Application No. 2020124652.
Office Action dated Dec. 11, 2020 in Russian Application No. 2020124653.
Office Action dated Jan. 22, 2021 in Russian Application No. 2020124657.
Office Action dated Jan. 22, 2021 in Russian Application No. 2020124658.
Extended European Search Report dated Dec. 18, 2020 in European Application No. 18775504.6.
Office Action dated Jan. 19, 2021 in Japanese Application No. 2019-553569.
Extended European Search Report dated Jan. 14, 2021 in European Application No. 18784738.9.
Extended European Search Report dated Dec. 10, 2020 in European Application No. 20188932.6.
Office Action dated Jan. 12, 2021 in Japanese Application No. 2019-555201.
Office Action dated Jan. 12, 2021 in Japanese Application No. 2019-555169.

(56) References Cited

OTHER PUBLICATIONS

Office Action dated Jan. 5, 2021 in Japanese Application No. 2019-558557.
Extended European Search Report dated Nov. 19, 2020 in European Application No. 20188792.4.
Office Action dated Dec. 1, 2020 in Japanese Application No. 2020-501188.
Extended European Search Report dated Dec. 18, 2020 in European Application No. 20188926.8.
Office Action dated Jan. 19, 2021 in Japanese Application No. 2020-501514.
Office Action dated Sep. 24, 2020 in Korean Application No. 10-2018-0012456.
Office Action dated May 28, 2020 in Korean Application No. 10-2017-0147605.
Office Action dated Apr. 2, 2019 in Korean Application No. 10-2019-0021286.
Office Action dated Apr. 3, 2019 in Korean Application No. 10-2019-0018812.
Office Action dated Apr. 4, 2019 in Korean Application No. 10-2019-0020484.
Office Action dated Apr. 4, 2019 in Korean Application No. 10-2019-0019194.
Communication dated May 27, 2020 by the Russian Patent Office in application No. 2019121813.
Communication dated Feb. 18, 2020 by the Russian Patent Office in application No. 2019121813.
Communication dated Jan. 15, 2021 by the European Patent Office in application No. 20188949.0.
International Search Report dated Nov. 14, 2018 from the International Searching Authority in International Application No. PCT/KR2018/004118.
International Search Report dated Nov. 6, 2018 from the International Searching Authority in International Application No. PCT/KR2018/004178.
International Search Report dated Sep. 7, 2018 from the International Searching Authority in International Application No. PCT/KR2018/004171.
International Search Report dated Sep. 7, 2018 from the International Searching Authority in International Application No. PCT/KR2018/004172.
International Search Report dated Nov. 6, 2018 from the International Searching Authority in International Application No. PCT/KR2018/004129.
Office Action dated Apr. 4, 2019 in Korean Application No. 10-2019-0019195.
International Search Report dated Nov. 6, 2018 from the International Searching Authority in International Application No. PCT/KR2018/004130.
International Search Report dated Septembers, 2018 from the International Searching Authority in International Application No. PCT/KR2018/004179.
Office Action dated Apr. 25, 2019 in Korean Application No. 10-2019-0033721.
International Search Report dated Nov. 26, 2018 from the International Searching Authority in International Application No. PCT/KR2018/009094.
International Search Report dated Feb. 28, 2019 from the International Searching Authority in International Application No. PCT/KR2018/009100.
International Search Report dated Jul. 24, 2018 from the International Searching Authority in International Application No. PCT/KR2018/003691.
International Search Report dated Septembers, 2018 from the International Searching Authority in International Application No. PCT/KR2018/004176.
Office Action dated Apr. 25, 2019 in Korean Application No. 10-2019-0033784.
Office Action dated Apr. 9, 2021 in Korean Application No. 10-2020-0116256.
Office Action dated May 5, 2021 in Canadian Application No. 3,047,236.
Extended European Search Report dated Apr. 1, 2021 in European Application No. 18805933.1.
Extended European Search Report dated Jun. 16, 2021 in European Application No. 18853434.1.
Extended European Search Report dated Jun. 14, 2021 in European Application No. 18842951.8.
Extended European Search Report dated Jan. 14, 2021 in European Application No. 18783776.0.
Extended European Search Report dated Jan. 25, 2021 in European Application No. 18785166.2.
Extended European Search Report dated Jan. 29, 2021 in European Application No. 18784464.2.
Extended European Search Report dated Mar. 15, 2021 in European Application No. 18785061.5.
Extended European Search Report dated Mar. 19, 2021 in European Application No. 18784164.8.
Extended European Search Report dated Mar. 24, 2021 in European Application No. 18784268.7.
Extended European Search Report dated Mar. 25, 2021 in European Application No. 18784370.1.
Extended European Search Report dated Mar. 25, 2021 in European Application No. 18784841.1.
Office Action dated Feb. 24, 2021 in Japanese Application No. 2019-555168.
Office Action dated Feb. 24, 2021 in Japanese Application No. 2019-555203.
Office Action dated Feb. 24, 2021 in Japanese Application No. 2019-555204.
Office Action dated Feb. 4, 2021 in Russian Application No. 2020124609.
Office Action dated Feb. 9, 2021 in Japanese Application No. 2019-555184.
Office Action dated Jan. 26, 2021 in Japanese Application No. 2020-501521.
Office Action dated Mar. 2, 2021 in Japanese Application No. 2019-555170.
Office Action dated Mar. 2, 2021 in Japanese Application No. 2019-555182.
Office Action dated Mar. 30, 2021 in Japanese Application No. 2020-501377.
Office Action dated Jan. 19, 2021 in Indonesian Application No. P00201906007.
Notification of Reason for Refusal dated Jul. 22, 2021 from the Korean Intellectual Property Office in KR Application No. 10-2021-0051359.
Office Action dated Jul. 27, 2021 from the China National Intellectual Property Administration in CN Application No. 201780084891.5.
Office Action dated Jun. 29, 2021 from the China National Intellectual Property Administration in CN Application No. 201880022072.2.
Office Action dated Aug. 16, 2021 from the China National Intellectual Property Administration in CN Application No. 201880024006.9.
Office Action dated Aug. 26, 2021 from the China National Intellectual Property Administration in CN Application No. 201880024107.6.
Office Action dated Jul. 26, 2021 from the China National Intellectual Property Administration in CN Application No. 201880024059.0.
Office Action dated Jul. 19, 2021 from the China National Intellectual Property Administration in CN Application No. 201880024070.7.
Extended European Search Report dated Jul. 1, 2021 from the European Patent Office in EP application No. 18854661.8.
Communication dated Aug. 4, 2021 by the Chinese Patent Office in Chinese Application No. 201880024289.7.
Communication dated Jul. 16, 2021 by the Chinese Patent Office in Chinese Application No. 201880024367.3.
Communication dated Sep. 17, 2021 by the Chinese Patent Office in Chinese Application No. 201880030699.2.

(56) References Cited

OTHER PUBLICATIONS

Office Action dated Sep. 29, 2021 in Chinese Application No. 201880024311.8.
Office Action dated Sep. 24, 2021 in Chinese Application No. 201880024010.5.
Office Action dated Sep. 29, 2021 in Chinese Application No. 201880024276.X.
Office Action dated Oct. 28, 2021 in Chinese Application No. 201880046418.2.
Extended European Search Report dated Oct. 27, 2021 in European Application No. 18844735.3.
Office Action dated Dec. 1, 2021 from the China Application No. 201880046367.3.
Office Action dated Nov. 25, 2021 from the China Application No. 201880047174.X.

\* cited by examiner

AEROSOL GENERATION DEVICE

This application is a continuation of U.S. application Ser. No. 16/644,654 filed on Mar. 5, 2020, which is a National Stage of International Application No. PCT/KR2018/006747 filed Jun. 15, 2018, claiming priorities based on Korean Patent Application Nos. 10-2017-0113954 filed Sep. 6, 2017 and 10-2018-0067035 filed Jun. 11, 2018.

TECHNICAL FIELD

The present disclosure relates to an aerosol generation device, and more particularly, to an aerosol generation device in which a fastening structure is concealed from exposure.

BACKGROUND ART

Recently, the demand for alternative methods to overcome the shortcomings of general cigarettes has increased. For example, there is a growing demand for a method of generating aerosol by heating an aerosol generating material, rather than burning cigarettes. Accordingly, studies on a heating-type cigarette or a heating-type aerosol generating device have been actively conducted.

When a heating-type aerosol generation device is used, a fastening structure that fastens components of the heating-type aerosol generation device may be exposed to the outside and damaged by an external pressure or stimulation. In addition, when a user arbitrarily disassembles or releases the exposed fastening structure of the aerosol generation device, the aerosol generation device may fail to operate properly.

A fastening structure according to the related art is formed on an outer portion of the aerosol generation device and is exposed to the outside, or even if a fastening structure is concealed, the concealed fastening structure is a simple structure that the user may arbitrarily and easily disassemble. In order to improve durability by preventing breakage or damage to the aerosol generation device, it is necessary to conceal the fastening structure such that the fastening structure of the aerosol generation device is not exposed to the outside.

In addition, in the structure of the aerosol generation device, it was difficult to discern whether the aerosol generation device was arbitrarily disassembled when the aerosol generation device was broken or damaged due to the arbitrary disassembly of the aerosol generation device by the user.

DETAILED DESCRIPTION

Technical Problem

Provided is an aerosol generation device in which a fastening structure is concealed from exposure to the outside. The technical problem of the present disclosure is not limited to the above-described technical problems, and other technical problems may be deduced from the following embodiments.

Solution to Problem

An aerosol generation device according to embodiments may include a first housing comprising an opening at one side, an inner space accommodating a cigarette inserted through the opening, and a heater disposed in the inner space; a second housing coupled to other side of the first housing and including a controller; a fastening portion configured to couple the first housing and the second housing; a battery coupled to the second housing; and a case coupled to the second housing for accommodating the second housing, the fastening portion, and the battery therein, wherein the fastening portion is prevented, by the case, from being exposed to outside.

The aerosol generation device may further include a coupling portion configured to couple the second housing and the case, and a cover mounted on one surface of the case to cover the coupling portion.

The aerosol generation device may further include an adhesive portion disposed between the case and the cover, and an adhesive material may be applied to both sides of the adhesive portion.

Based on the cover coupled to the case by the adhesive portion being separated from the case, a predetermined marking may occur on the adhesive portion.

The first housing may further include a flange formed at an end portion of the first housing, and the fastening portion may include a first groove portion extending from the flange toward the second housing, a second groove portion corresponding to the first groove portion and formed in the second housing, and a fastening means configured to fasten the first groove portion and the second groove portion.

The fastening means may include a pin, a screw, or a rivet.

The fastening portion of the aerosol generation device according to exemplary embodiments may include a hook portion extending from the first housing toward the second housing and an accommodation portion formed in the second housing to accommodate the hook portion.

The coupling portion may include a first coupling hole formed on one surface of the second housing, a second coupling hole corresponding to the first coupling hole and formed on the case, and a coupling means configured to couple the first coupling hole and the second coupling hole.

The coupling means may include a pin, a screw, or a rivet.

The first housing may further include a switch connected to the controller on an outer surface of the first housing, and the case may include a through hole exposing the switch to an outside.

The aerosol generation device may further include a cap portion accommodating the first housing therein.

A method of assembling an aerosol generation device according to exemplary embodiments may include providing a first housing comprising an opening in an upper portion, an inner space into which a cigarette may be inserted through the opening, and a heater disposed in the inner space; coupling a second housing comprising a controller to a lower portion of the first housing; coupling the first housing and the second housing through a fastening portion; coupling a battery to the second housing, and coupling a case to the second housing to accommodate the second housing, the fastening portion, and the battery therein, wherein an exposure of the fastening portion to an outside is prevented by the case.

Advantageous Effects

A case may include a cavity therein to accommodate a second housing, a battery, and a fastening portion. The second housing, the battery, and the fastening portion may be accommodated in the cavity therein to prevent exposure of the second housing, the battery, and the fastening portion.

Because the exposure of the fastening portion is prevented, a general access to the fastening portion by a user of an aerosol generation device may be prevented. Accordingly, the user of the aerosol generation device may not release or disassemble the aerosol generation device using a general method, and thus an arbitrary disassembly of the aerosol generation device may be prevented.

BEST MODE

An aerosol generation device according to an embodiment may include a first housing comprising an opening opened at one side, an inner space accommodating a cigarette inserted through the opening, and a heater positioned in the inner space; a second housing comprising a controller and coupled to other side of the first housing; a fastening portion configured to couple the first housing and the second housing; a battery coupled to the second housing; and a case accommodating the second housing, the fastening portion, and the battery therein and coupled to the second housing.

Mode of Disclosure

With respect to the terms in the various embodiments, the general terms which are currently and widely used are selected in consideration of functions of structural elements in the various embodiments of the present disclosure. However, meanings of the terms can be changed according to intention, a judicial precedence, an appearance of a new technology, and the like. In addition, in certain cases, a term which is not commonly used can be selected. In such a case, the meaning of the term will be described in detail in the description of the present disclosure. Therefore, the terms used in the various embodiments of the present disclosure should be defined based on the meanings of the terms and the descriptions provided herein.

In addition, unless explicitly described otherwise, the word "comprise" and variations such as "comprises" or "comprising" will be understood to imply the inclusion of stated elements but not the exclusion of any other elements. In addition, the terms "-er", "-or", and "module" described in the disclosure mean units for processing at least one function and operation and can be implemented by hardware components or software components and combinations thereof.

Hereinafter, the present disclosure will now be described more fully with reference to the accompanying drawings, in which embodiments of the present disclosure are shown such that one of ordinary skill in the art may easily understand the present disclosure. The disclosure may, however, be embodied in many different forms and should not be construed as being limited to the embodiments set forth herein.

Hereinafter, embodiments of the present disclosure will be described in detail with reference to the drawings.

Figure 1:
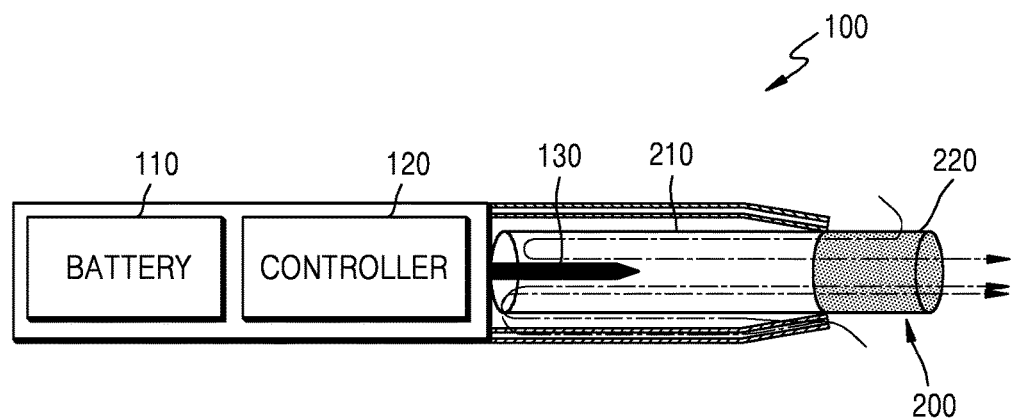
FIGS. 1 through 3 are diagrams showing examples in which a cigarette is inserted into an aerosol generating device.
Figure 2:
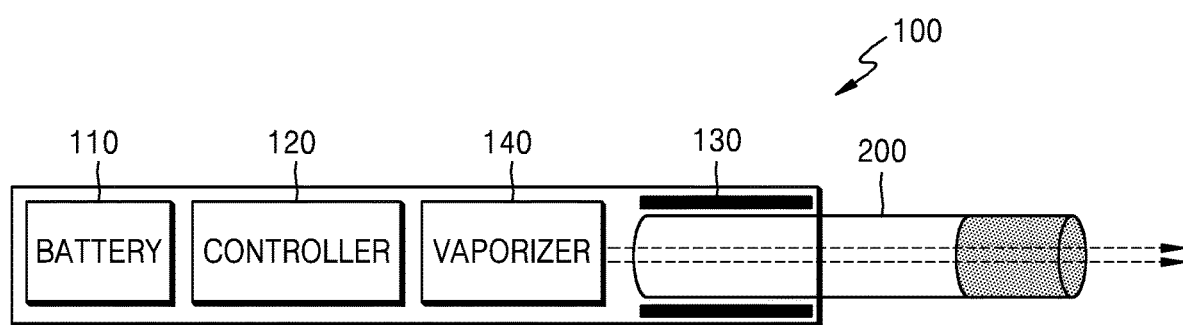
Figure 3:
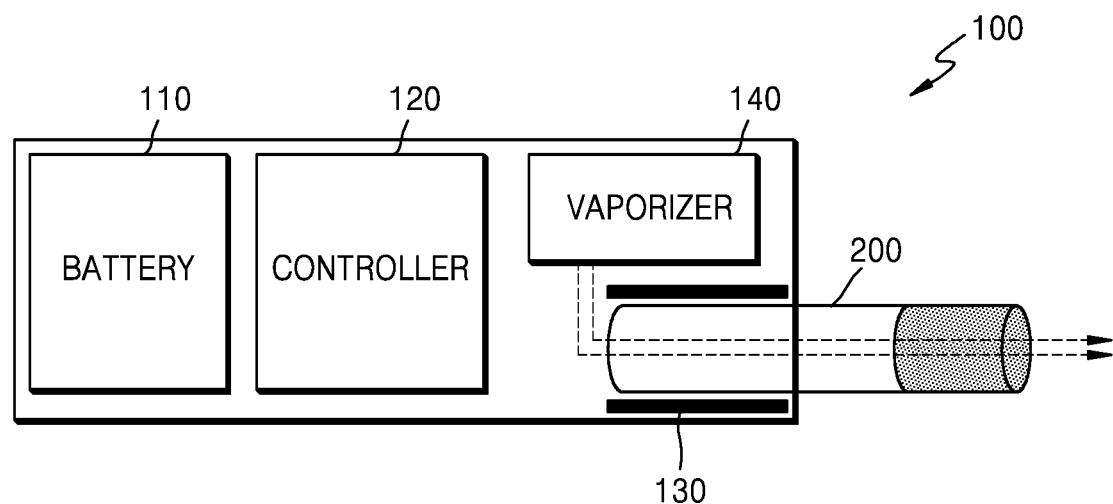

FIGS. 1 through 3 are diagrams showing examples in which a cigarette is inserted into an aerosol generating device.

Referring to FIG. 1, the aerosol generating device 100 may include a battery 110, a controller 120, and a heater 130. Referring to FIGS. 2 and 3, the aerosol generating device 100 may further include a vaporizer 140. Also, the cigarette 200 may be inserted into an inner space of the aerosol generating device 100.

FIGS. 1 through 3 illustrate components of the aerosol generating device 100, which are related to the present embodiments. Therefore, it will be understood by one of ordinary skill in the art related to the present embodiment that other general-purpose components may be further included in the aerosol generating device 100, in addition to the components illustrated in FIGS. 1 through 3.

Also, FIGS. 2 and 3 illustrate that the aerosol generating device 100 includes the heater 130. However, according to necessity, the heater 130 may be omitted.

FIG. 1 illustrates that the battery 110, the controller 120, and the heater 130 are arranged in series. Also, FIG. 2 illustrates that the battery 110, the controller 120, the vaporizer 140, and the heater 130 are arranged in series. Also, FIG. 3 illustrates that the vaporizer 140 and the heater 130 are arranged in parallel. However, the internal structure of the aerosol generating device 100 is not limited to the structures illustrated in FIGS. 1 through 3. In other words, according to the design of the aerosol generating device 100, the battery 110, the controller 120, the heater 130, and the vaporizer 140 may be differently arranged.

When the cigarette 200 is inserted into the aerosol generating device 100, the aerosol generating device 100 may operate the heater 130 and/or the vaporizer 140 to generate an aerosol from the cigarette 200 and/or the vaporizer 140. The aerosol generated by the heater 130 and/or the vaporizer 140 is delivered to a user by passing through the cigarette 200.

According to necessity, even when the cigarette 200 is not inserted into the aerosol generating device 100, the aerosol generating device 100 may heat the heater 130.

The battery 110 may supply power to be used for the aerosol generating device 100 to operate. For example, the battery 110 may supply power to heat the heater 130 or the vaporizer 140, and may supply power for operating the controller 120. Also, the battery 110 may supply power for operations of a display, a sensor, a motor, etc. mounted in the aerosol generating device 100.

The controller 120 may generally control operations of the aerosol generating device 100. Specifically, the controller 120 may control not only operations of the battery 110, the heater 130, and the vaporizer 140, but also operations of other components included in the aerosol generating device 100. Also, the controller 120 may check a state of each of the components of the aerosol generating device 100 to determine whether or not the aerosol generating device 100 is able to operate.

The controller 120 may include at least one processor. A processor may be implemented as an array of a plurality of logic gates or may be implemented as a combination of a general-purpose microprocessor and a memory in which a program executable in the microprocessor is stored. It will be understood by one of ordinary skill in the art that the processor may be implemented in other forms of hardware.

The heater 130 may be heated by the power supplied from the battery 110. For example, when the cigarette 200 is inserted into the aerosol generating device 100, the heater 130 may be located outside the cigarette 200. Thus, the heated heater 130 may increase temperature of an aerosol generating material in the cigarette 200.

The heater 130 may include an electro-resistive heater. For example, the heater 130 may include an electrically conductive track, and the heater 130 may be heated when currents flow through the electrically conductive track. However, the heater 130 is not limited to the examples described above and may include all heaters which may be heated to a desired temperature. Here, the desired temperature may be pre-set in the aerosol generating device 100 or may be set as a temperature desired by a user.

As another example, the heater 130 may include an induction heater. Specifically, the heater 130 may include an electrically conductive coil for heating a cigarette in an induction heating method, and the cigarette may include a susceptor which may be heated by the induction heater.

For example, the heater 130 may include a tube-type heating element, a plate-type heating element, a needle-type heating element, or a rod-type heating element, and may heat the inside or the outside of the cigarette 200, according to the shape of the heating element.

Also, the aerosol generating device 100 may include a plurality of heaters 130. Here, the plurality of heaters 130 may be inserted into the cigarette 200 or may be arranged outside the cigarette 200. Also, some of the plurality of heaters 130 may be inserted into the cigarette 200 and the others may be arranged outside the cigarette 200. In addition, the shape of the heater 130 is not limited to the shapes illustrated in FIGS. 1 through 3 and may include various shapes.

The vaporizer 140 may generate an aerosol by heating a liquid composition and the generated aerosol may pass through the cigarette 200 to be delivered to a user. In other words, the aerosol generated via the vaporizer 140 may move along an air flow passage of the aerosol generating device 100 and the air flow passage may be configured such that the aerosol generated via the vaporizer 140 passes through the cigarette 200 to be delivered to the user.

For example, the vaporizer 140 may include a liquid storage, a liquid delivery element, and a heating element, but it is not limited thereto. For example, the liquid storage, the liquid delivery element, and the heating element may be included in the aerosol generating device 100 as independent modules.

The liquid storage may store a liquid composition. For example, the liquid composition may be a liquid including a tobacco-containing material having a volatile tobacco flavor component, or a liquid including a non-tobacco material. The liquid storage may be formed to be detachable from the vaporizer 140 or may be formed integrally with the vaporizer 140.

For example, the liquid composition may include water, a solvent, ethanol, plant extract, spices, flavorings, or a vitamin mixture. The spices may include menthol, peppermint, spearmint oil, and various fruit-flavored ingredients, but are not limited thereto. The flavorings may include ingredients capable of providing various flavors or tastes to a user. Vitamin mixtures may be a mixture of at least one of vitamin A, vitamin B, vitamin C, and vitamin E, but are not limited thereto. Also, the liquid composition may include an aerosol forming substance, such as glycerin and propylene glycol.

The liquid delivery element may deliver the liquid composition of the liquid storage to the heating element. For example, the liquid delivery element may be a wick such as cotton fiber, ceramic fiber, glass fiber, or porous ceramic, but is not limited thereto.

The heating element is an element for heating the liquid composition delivered by the liquid delivery element. For example, the heating element may be a metal heating wire, a metal hot plate, a ceramic heater, or the like, but is not limited thereto. In addition, the heating element may include a conductive filament such as nichrome wire and may be positioned as being wound around the liquid delivery element. The heating element may be heated by a current supply and may transfer heat to the liquid composition in contact with the heating element, thereby heating the liquid composition. As a result, aerosol may be generated.

For example, the vaporizer 140 may be referred to as a cartomizer or an atomizer, but it is not limited thereto.

The aerosol generating device 100 may further include general-purpose components in addition to the battery 110, the controller 120, the heater 130, and the vaporizer 140. For example, the aerosol generating device 100 may include a display capable of outputting visual information and/or a motor for outputting haptic information. Also, the aerosol generating device 100 may include at least one sensor (a puff detecting sensor, a temperature detecting sensor, a cigarette insertion detecting sensor, etc.). Also, the aerosol generating device 100 may be formed as a structure where, even when the cigarette 200 is inserted into the aerosol generating device 100, external air may be introduced or internal air may be discharged.

Although not illustrated in FIGS. 1 through 3, the aerosol generating device 100 and an additional cradle may form together a system. For example, the cradle may be used to charge the battery 110 of the aerosol generating device 100. Alternatively, the heater 130 may be heated when the cradle and the aerosol generating device 100 are coupled to each other.

The cigarette 200 may be similar as a general combustive cigarette. For example, the cigarette 200 may be divided into a first portion including an aerosol generating material and a second portion including a filter, etc. Alternatively, the second portion of the cigarette 200 may also include an aerosol generating material. For example, an aerosol generating material made in the form of granules or capsules may be inserted into the second portion.

The entire first portion may be inserted into the aerosol generating device 100, and the second portion may be exposed to the outside. Alternatively, only a portion of the first portion may be inserted into the aerosol generating device 100, or the entire first portion and a portion of the second portion may be inserted into the aerosol generating device 100. The user may puff aerosol while holding the second portion by the mouth of the user. In this case, the aerosol is generated by the external air passing through the first portion, and the generated aerosol passes through the second portion and is delivered to the user's mouth.

For example, the external air may flow into at least one air passage formed in the aerosol generating device 100. For example, the opening and closing and/or a size of the air passage formed in the aerosol generating device 100 may be adjusted by the user. Accordingly, the amount of smoke and a smoking satisfaction may be adjusted by the user. As another example, the external air may flow into the cigarette 200 through at least one hole formed in a surface of the cigarette 200.

Hereinafter, an example of the cigarette 200 will be described with reference to FIG. 4.

Figure 4:
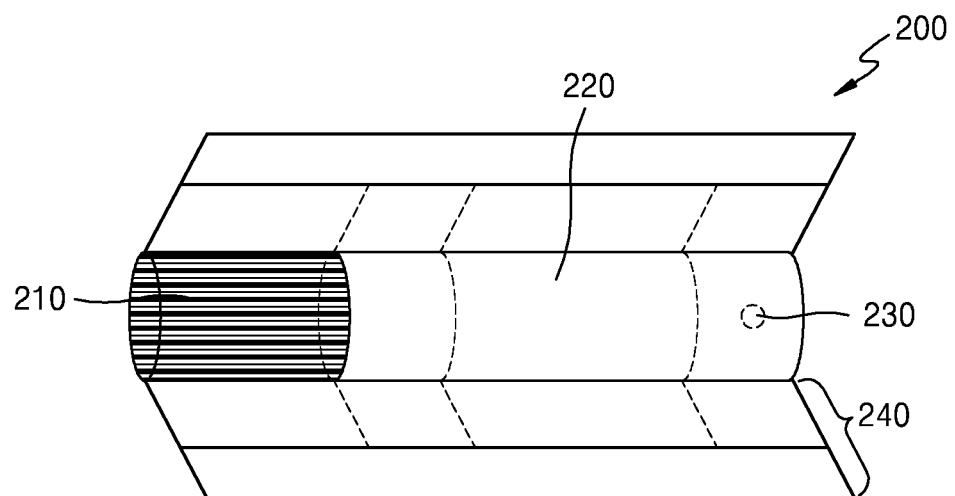
FIG. 4 illustrates an example of a cigarette.

FIG. 4 illustrates an example of a cigarette.

Referring to FIG. 4, the cigarette 200 may include a tobacco rod 210 and a filter rod 220. The first portion 210 described above with reference to FIGS. 1 through 3 may include the tobacco rod, and the second portion may include the filter rod 220.

FIG. 4 illustrates that the filter rod 220 includes a single segment. However, the filter rod 220 is not limited thereto. In other words, the filter rod 220 may include a plurality of segments. For example, the filter rod 220 may include a first segment configured to cool an aerosol and a second segment configured to filter a certain component included in the aerosol. Also, according to necessity, the filter rod 220 may further include at least one segment configured to perform other functions.

The cigarette 200 may be packaged via at least one wrapper 240. The wrapper 240 may have at least one hole through which external air may be introduced or internal air may be discharged. For example, the cigarette 200 may be packaged via one wrapper 240. As another example, the cigarette 200 may be double-packaged via at least two wrappers 240. For example, the tobacco rod 210 may be packaged via a first wrapper, and the filter rod 220 may be packaged via a second wrapper. Also, the tobacco rod 210 and the filter rod 220, which are respectively packaged via separate wrappers, may be coupled to each other, and the entire cigarette 200 may be packaged via a third wrapper. When each of the tobacco rod 210 and the filter rod 220 includes a plurality of segments, each segment may be packaged via a separate wrapper. Also, the entire cigarette 200 including the plurality of segments, which are respectively packaged via the separate wrappers and which are coupled to each other, may be re-packaged via another wrapper.

The tobacco rod 210 may include an aerosol generating material. For example, the aerosol generating material may include at least one of glycerin, propylene glycol, ethylene glycol, dipropylene glycol, diethylene glycol, triethylene glycol, tetraethylene glycol, and oleyl alcohol, but it is not limited thereto. Also, the tobacco rod 210 may include other additives, such as flavors, a wetting agent, and/or organic acid. Also, the tobacco rod 210 may include a flavored liquid, such as menthol or a moisturizer, which is injected to the tobacco rod 210.

The tobacco rod 210 may be manufactured in various forms. For example, the tobacco rod 210 may be formed as a sheet or a strand. Also, the tobacco rod 210 may be formed as a pipe tobacco, which is formed of tiny bits cut from a tobacco sheet. Also, the tobacco rod 210 may be surrounded by a heat conductive material. For example, the heat-conducting material may be, but is not limited to, a metal foil such as aluminum foil. For example, the heat conductive material surrounding the tobacco rod 210 may uniformly distribute heat transmitted to the tobacco rod 210, and thus, the heat conductivity applied to the tobacco rod may be increased and taste of the tobacco may be improved. Also, the heat conductive material surrounding the tobacco rod 210 may function as a susceptor heated by the induction heater. Here, although not illustrated in the drawings, the tobacco rod 210 may further include an additional susceptor, in addition to the heat conductive material surrounding the tobacco rod 210.

The filter rod 220 may include a cellulose acetate filter. Also, the shapes of the filter rod 220 are not limited. For example, the filter rod 220 may include a cylinder-type rod or a tube-type rod having a hollow inside. Also, the filter rod 220 may include a recess-type rod. When the filter rod 220 includes a plurality of segments, at least one of the plurality of segments may have a different shape.

The filter rod 220 may be formed to generate flavors. For example, a flavoring liquid may be injected into the filter rod 220, or an additional fiber coated with a flavoring liquid may be inserted into the filter rod 220.

Also, the filter rod 220 may include at least one capsule 230. Here, the capsule 230 may generate a flavor or an aerosol. For example, the capsule 230 may have a configuration in which a liquid containing a flavoring material is wrapped with a film. For example, the capsule 230 may have a spherical or cylindrical shape, but is not limited thereto.

When the filter rod 220 includes a segment configured to cool the aerosol, the cooling segment may include a polymer material or a biodegradable polymer material. For example, the cooling segment may include pure polylactic acid alone, but the material for forming the cooling segment is not limited thereto. In some embodiments, the cooling segment may include a cellulose acetate filter having a plurality of holes. However, the cooling segment is not limited to the above-described example and is not limited as long as the cooling segment cools the aerosol.

Although not illustrated in FIG. 4, the cigarette 200 according to an embodiment may further include a front-end filter. The front-end filter may be located on a side of the tobacco rod 210, the side facing the filter rod 220. The front-end filter may prevent the tobacco rod 210 from being detached outwards and prevent a liquefied aerosol from flowing into the aerosol generating device 100 (FIGS. 1 through 3) from the tobacco rod 210, during smoking.

Figure 5A:
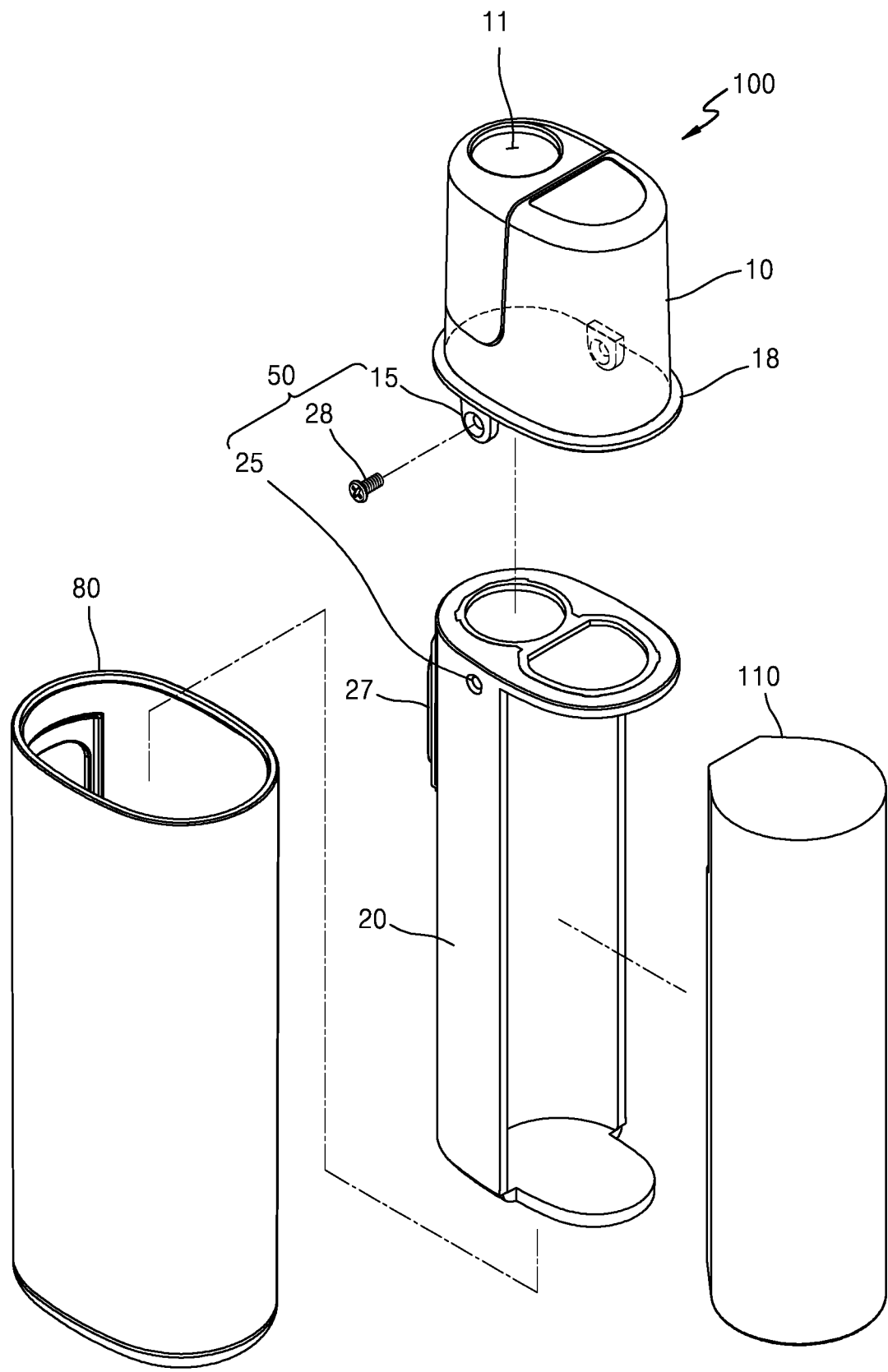
FIG. 5A is an exploded view of an aerosol generation device according to an embodiment.
Figure 5B:
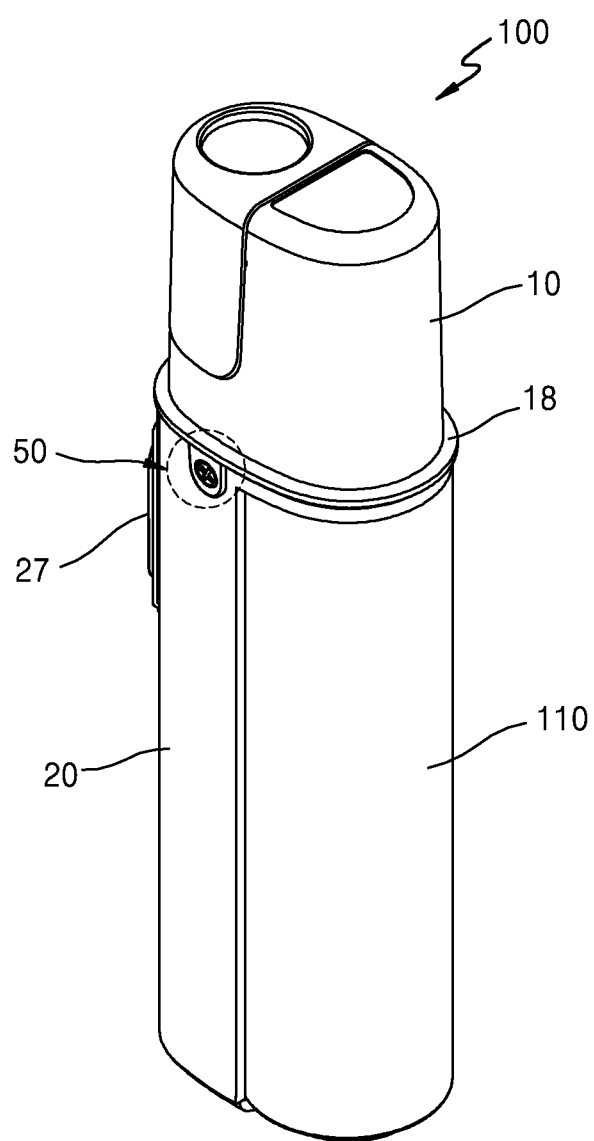
FIG. 5B is a perspective view of the aerosol generation device according to an embodiment shown in FIG. 5A.

FIG. 5A is an exploded view of an aerosol generation device 100 according to an embodiment, and FIG. 5B is a perspective view of the aerosol generation device 100 according to an embodiment shown in FIG. 5A.

The aerosol generation device 100 according to an embodiment shown in FIGS. 5A and 5B may include a first housing 10, a second housing 20, a fastening portion 50, and a case 80.

The first housing 10 of the aerosol generation device 100 may include an opening 11 at one side and accommodate the cigarette 200 (see FIG. 1) inserted through the opening 11. The first housing 10 may also include an inner space in which the inserted cigarette is accommodated and the heater 130 (see FIG. 1) which heats the cigarette in the inner space.

The aerosol generation device 100 may include a second housing 20 coupled to other side of the first housing 10. The second housing 20 may be coupled to the other side of the first housing 10 opposite to the one side of the first housing 10 into which the cigarette is inserted.

The second housing 20 may include the controller 120 (see FIG. 4) inside the second housing 20. The second housing 20 may also include, in one side of the second housing 20, a switch 27 connected to the controller to transmit a signal to the controller 120.

The aerosol generation device 100 may include the fastening portion 50 coupling the first housing 10 and the second housing 20. The second housing 20 may be coupled to the other side of the first housing 10 through the fastening portion 50 and may be in contact with at least part of the first housing 10.

The aerosol generation device 100 may further include a battery 110 coupled to the second housing 20. The battery 110 may be coupled to one surface of the second housing 20 and may be positioned at the other side of the first housing 10. The battery 110 may have, for example, a shape surrounding one side of the second housing 20, but is not limited thereto. The battery 110 may also be integrally coupled to the second housing 20 and may provide power to the second housing 20 to operate the controller inside the second housing 20.

The aerosol generation device 100 may include the case 80 that accommodates the second housing 20, the fastening portion 50, and the battery 110 therein and coupled to the second housing 20. Because the case 80 accommodates all of the second housing 20, the fastening portion 50, and the battery 110 therein, the second housing 20, the fastening portion 50, and the battery 110 may be prevented from being exposed to the outside and may be concealed by the case 80.

Because the fastening portion 50 coupling the first housing 10 and the second housing 20 is concealed by the case 80, a user of the aerosol generation device 100 may not release or separate coupling of the first housing 10 and the second housing 20 by a general access, thereby preventing breakage of the aerosol generation device 100.

The fastening portion 50 of the aerosol generation device 100 according to exemplary embodiments may be described in more detail with reference to FIGS. 5A and 5B.

The first housing 10 of the aerosol generation device 100 may include a flange 18 formed at other end portion of the first housing 10. The flange 18 may extend in the circumferential direction at the other end portion of the first housing 10 and may protrude in the circumferential direction at the other end portion of the first housing 10 to form a stepped portion.

The fastening portion 50 may include a first groove portion 15 protruding from the flange 18 toward the second housing 20, a second groove portion 25 corresponding to the first groove portion 15 and formed in the second housing 20, and a fastening means 28 fastening the first groove portion 15 and the second groove portion 25.

When the first groove portion 15 protrudes from the flange 18 toward the second housing 20 and when the first housing 10 and the second housing 20 are coupled, the first groove portion 15 may be position on an outer surface of the second housing 20.

The second groove portion 25 may be formed in the second housing 20 to correspond to a position of the first groove portion 15. For example, the first groove portion 15 and the second groove portion 25 may have the same central axis when coupled such that the fastening means 28 may pass through the first groove portion 15 and the second groove portion 25 together.

The first groove portion 15 may be plural. For example, the first groove portions 15 may be symmetrically formed on the flange 18 of the first housing 10 with respect to the center of the flange 18 in the circumferential direction of the first housing 20. The second groove portion 25 may be plural so as to correspond to the first groove portion 15, and may be formed at a position in the second housing where the first groove portion 15 extends. When a plurality of first groove portions 15 and a plurality of second groove portions 25 are installed, the first groove portions 15 and the second groove portions 25 may be spaced apart from each other along the extending direction of the flange 18.

The fastening means 28 may pass through the first groove portion 15 and the second groove portion 25 to fasten the first groove portion 15 and the second groove portion 25, and the fastening means 28 may be, for example, a pin, a screw, or a rivet. The first groove portion 15 and the second groove portion 25 may be coupled by the fastening means 28 and may vary in size or shape according to the fastening means 28.

For example, when the fastening means 28 is the screw, the first groove portion 15 and the second groove portion 25 may have a shape including a screw thread inside the first groove portion 15 and the second groove portion 25, respectively, so as to accommodate the screw that is the fastening means 28.

When the first housing 10 and the second housing 20 are coupled by the fastening means 28 fastening the first groove portion 15 and the second groove portion 25, the heater 130 in the first housing 10 may be electrically connected to the controller 120 in the second housing 20. Accordingly, the heater 130 of the first housing 10 may be controlled by the controller 120 of the second housing 20.

When smoking, the user may operate the aerosol generation device 100 by pressing the switch 27 formed on one surface of the second housing 20 to transmit the signal to the controller 120.

Figure 6A:
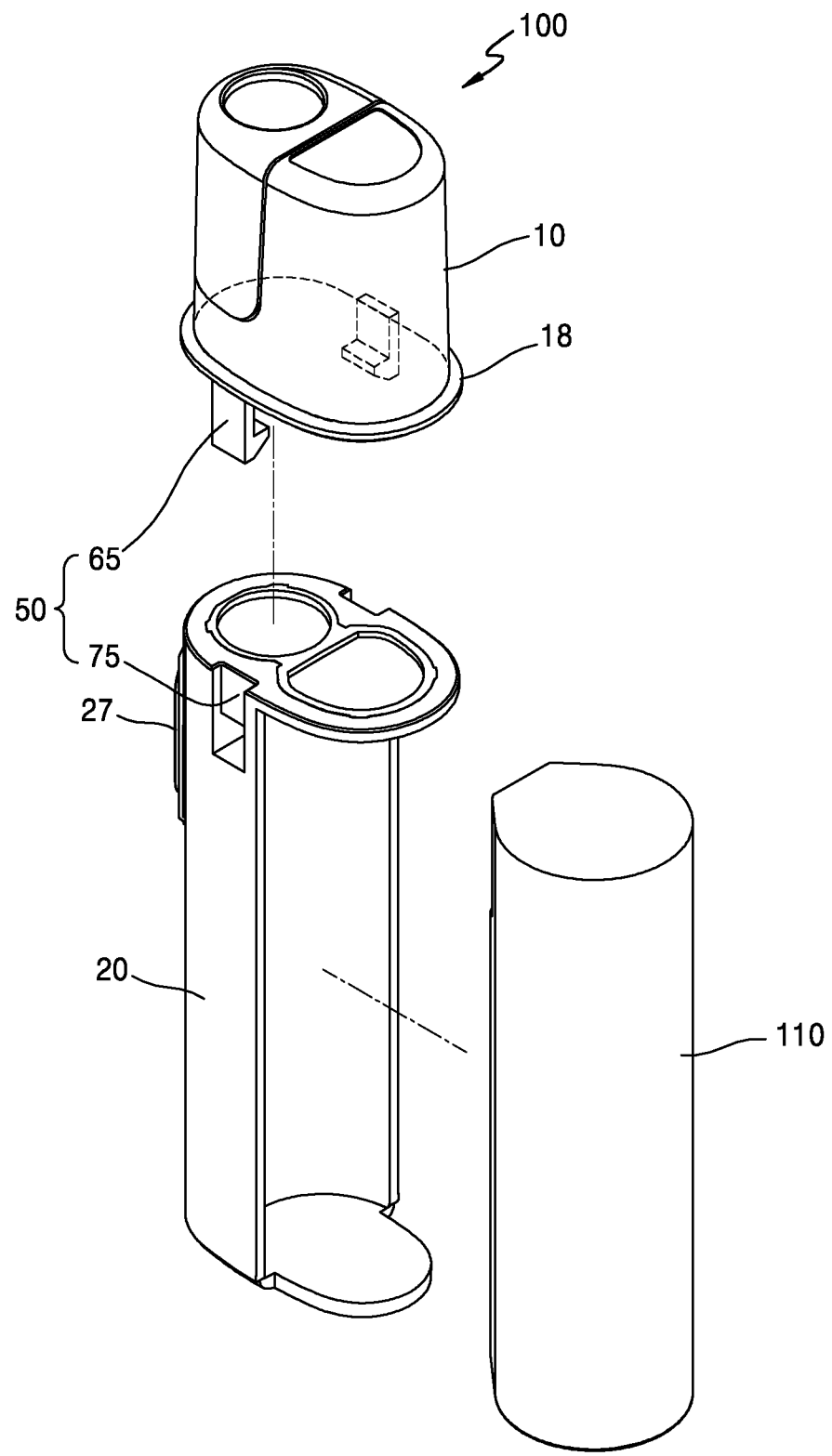
FIG. 6A is an exploded view of an aerosol generation device according to another embodiment.
Figure 6B:
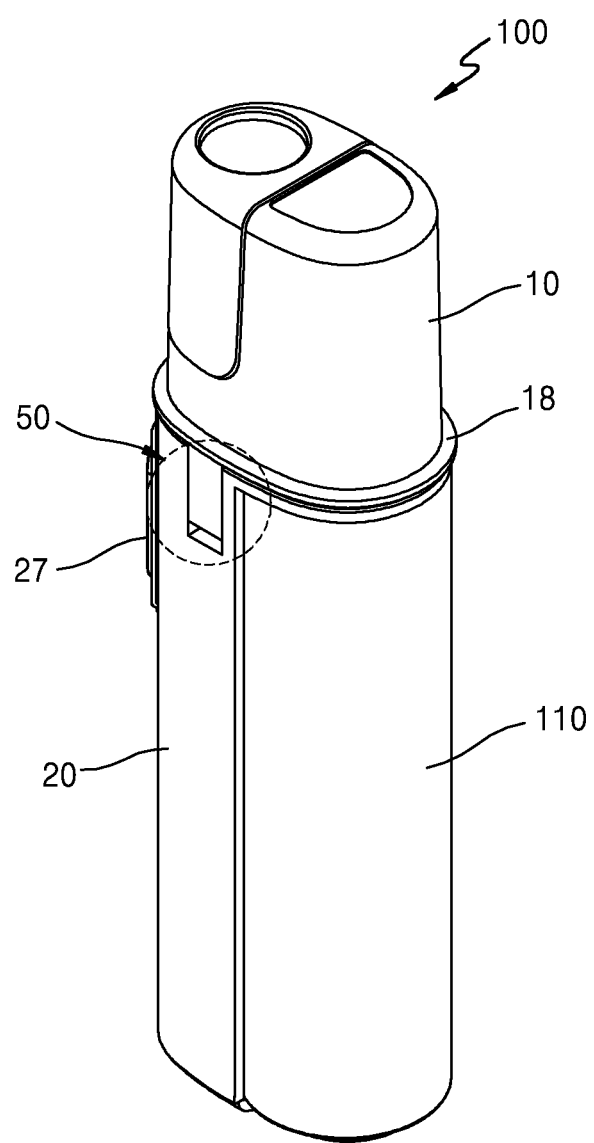
FIG. 6B is a perspective view of the aerosol generation device according to another embodiment shown in FIG. 6A.

FIG. 6A is an exploded view of the aerosol generation device 100 according to an embodiment, and FIG. 6B is a perspective view of the aerosol generation device 100 according to an embodiment shown in FIG. 6A.

The fastening portion 50 of the aerosol generation device 100 according to an embodiment may be described in more detail with reference to FIGS. 6A and 6B.

The first housing 10 of the aerosol generation device 100 may include the flange 18 formed at the other end portion of the first housing 10. The fastening portion 50 may include a hook portion 65 extending from the flange 18 and extending toward the second housing 20, and an accommodation portion 75 formed in the second housing 20 to accommodate the hook portion 65.

The hook portion 65 may protrude from the flange 18 of the first housing 10 toward the second housing 20 such that the hook portion 65 is positioned on an outer surface of the second housing 20 when the first housing 10 is coupled to the second housing 20.

Alternatively, the hook portion 65 may protrude toward the inside of the second housing 20 such that the hook portion 65 is positioned on an inner surface of the second housing 20 when the first housing 10 is coupled to the second housing 20.

The hook portion 65 may include a protrusion portion having a ring shape at the end of the hook portion 65, but the embodiments are not limited by a specific configuration of the hook portion 65.

For example, the end of the hook portion 65 may be positioned on the outer surface of the second housing 20 and the protrusion portion of the hook portion 65 may be the protrusion portion having the ring shape extending in a direction of the outer surface of the second housing 20. The hook portion 65 may be coupled to the accommodation portion 75 formed on the outer surface of the second housing 20 through the protrusion portion having the ring shape.

As another example, the hook portion 65 may extend into the second housing 20 to engage with the inner surface of the second housing 20. The protrusion portion formed at the end of the hook portion 65 may have the ring shape and extend in a direction of the inner surface of the second housing 20.

The protrusion portion formed at the end of the hook portion 65 may be directly fastened with the accommodation portion 75 formed in the second housing 20. The hook portion 65 accommodated in the accommodation portion 75 of the second housing 20 may be decoupled from the second housing 20 when a force greater than a predetermined range is applied.

The accommodating portion 75 formed in the second housing 20 may be formed in the outer surface or the inner surface of the second housing 20 to correspond to the hook portion 65 of the first housing 10. The accommodating portion 75 may have a shape that may accommodate the protrusion portion of the end of the hook portion 65. For example, when the shape of the protruding portion of the end of the hook portion 65 has the ring shape, the accommodating portion 75 may have the shape that may be engaged with the ring shape. In addition, when the hook portion 65 of the first housing 10 and the accommodation portion 75 of the second housing 20 are coupled inside the second housing 20, the hook portion 65 and the accommodation portion 75 may be concealed from the outside.

Figure 7A:
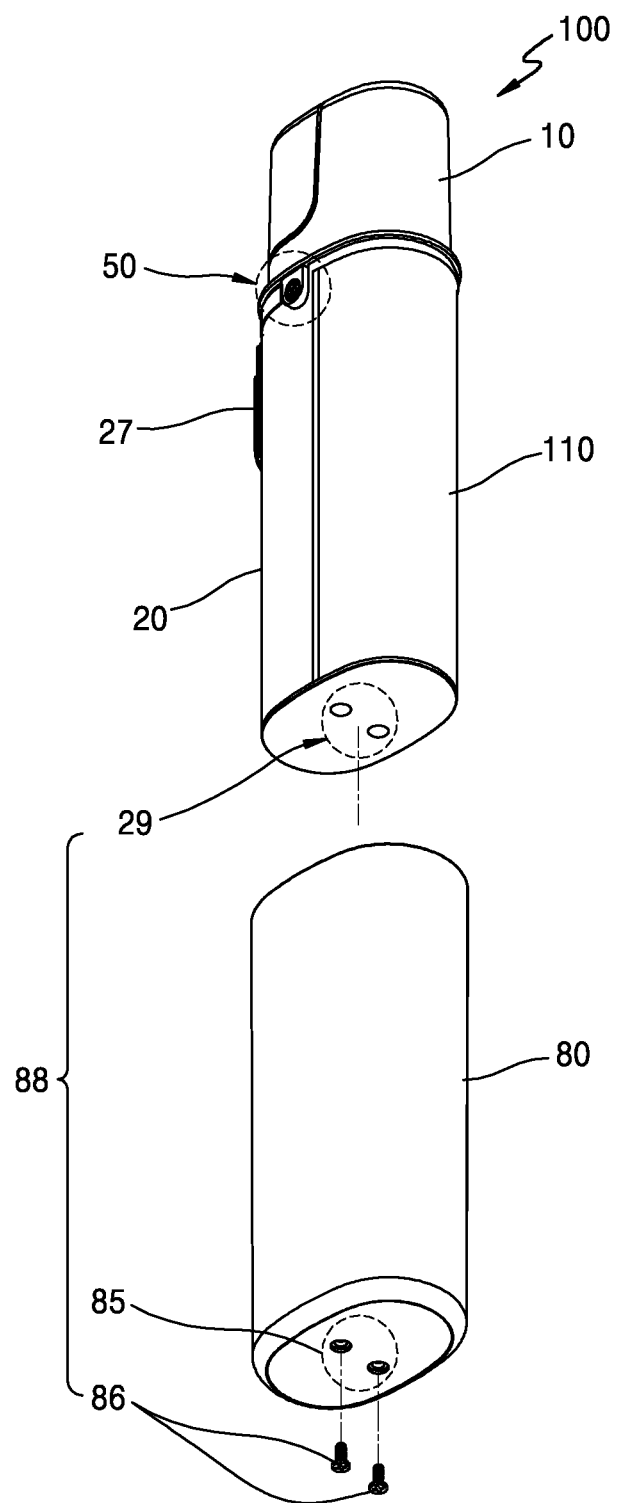
FIG. 7A is a perspective view of an aerosol generation device to which a case is coupled according to an embodiment.

FIG. 7A is a perspective view of the aerosol generation device 100 to which the case 80 is coupled according to an embodiment.

Referring to FIG. 7A, the aerosol generation device 100 may include the case 80 that accommodates the second housing 20, the battery 110, and the fastening portion 50 of the aerosol generation device 100 therein and coupled to the second housing 20.

The case 80 may include a cavity therein to accommodate the second housing 20, the battery 110, and the fastening portion 50. The second housing 20, the battery 110, and the fastening portion 50 may be accommodated in the cavity therein to prevent exposure of the second housing 20, the battery 110, and the fastening portion 50.

Because the exposure of the fastening portion 50 is prevented, a general access to the fastening portion 50 by a user of the aerosol generation device 100 may be prevented. Accordingly, the user of the aerosol generation device 100 may not release or disassemble the aerosol generation device 100 using a general method, and thus an arbitrary disassembly of the aerosol generation device 100 may be prevented.

The case 80 may be coupled to the second housing 20 through a coupling portion 88. Here, the coupling portion 88 may include a first coupling hole 29 formed in one surface of the second housing 20, a second coupling hole 85 corresponding to the first coupling hole 29 and formed in the case 80, and coupling means 86 coupling the first coupling hole 29 and the second coupling hole 85.

The first coupling hole 29 may be formed in the other side of the second housing 20. The first coupling hole 29 may be formed in plural in the other side of the second housing 20 and may be, for example, two symmetrical grooves disposed to be symmetrical with respect to the center of the other side of the second housing 20.

The second coupling hole 85 may be formed in the other side of the case 80, and may be formed at a position corresponding to the first coupling hole 29 of the second housing 20 when the case 80 is coupled to the housing 20 while accommodating the second housing 20, the fastening portion 50, and the battery 110. For example, when the case 80 is coupled, the first coupling hole 29 and the second coupling hole 85 may have the same central axis such that the coupling means 86 may pass through the first coupling hole 29 and the second coupling hole 85 together.

The coupling means 86 may pass through the first coupling hole 29 and the second coupling hole 85 to fasten the first coupling hole 29 and the second coupling hole 85, and the coupling means 86 may be, for example, a pin, a screw, or a rivet. The first coupling hole 29 and the second coupling hole 85 may be coupled by the coupling means 86 and may vary in size or shape according to the coupling means 86.

For example, when the coupling means 86 is the screw, the first coupling hole 29 and the second coupling hole 85 may have a shape including a screw thread inside the first coupling hole 29 and the second coupling hole 85, respectively, so as to accommodate the screw that is the coupling means 86.

The case 80 may include a through hole 83 to expose the switch 27 formed on one side of the second housing 20 to the outside. The through hole 83 may be formed to correspond to the position and shape of the switch 27 and may be formed on one side of the case 80.

The switch 27 may be exposed to the outside through the through hole 83 such that a general access of the user may be easy. The switch 27 may be electrically connected to the controller 120 inside the second housing 20 to operate the controller 120. Therefore, when smoking, the user may operate the aerosol generation device 100 through the switch 27.

Figure 7B:
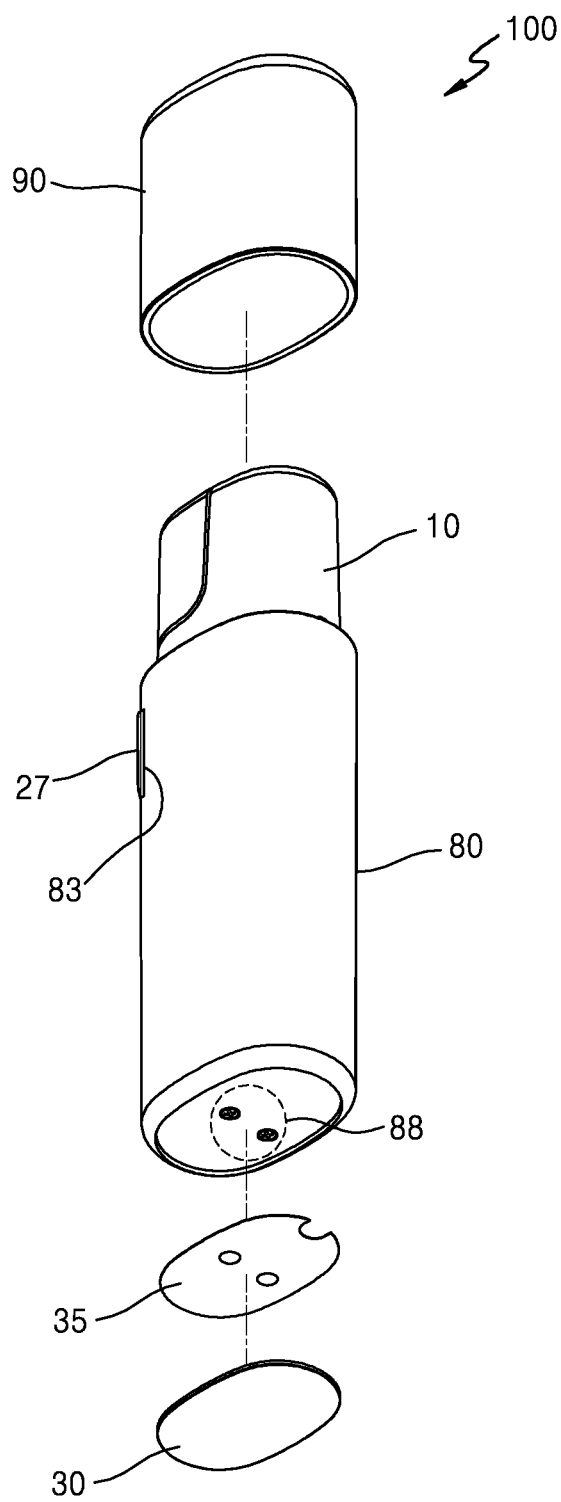
FIG. 7B is a diagram illustrating an aerosol generation device further including a cover and a cap portion according to an embodiment.

FIG. 7B is a diagram illustrating the aerosol generation device 100 further including a cover 30 and a cap portion 90 according to an embodiment.

The aerosol generation device 100 may further include the cap portion 90 disposed outside the first housing 10 of the aerosol generation device 100, surrounding the first housing 10 and having an end portion contacting the flange 18. The cap portion 90 may have an inner cavity that accommodates the first housing 10 therein. When the cap portion 90 is coupled to the aerosol generation device 100 surrounding the first housing 10, the end portion of the cap portion 90 may contact the flange 18 of the aerosol generation device 100.

The cap portion 90 accommodates the first housing 10 therein and is coupled to the flange 18 of the first housing 10 so as to be separable by an external force of the user of the aerosol generation device 100. Here, the cap portion 90 may be easily separated from the first housing 10 by the external force of the user. The first housing 10 and the cap portion 90 may include a binding means in which attraction is applied to each other.

The binding means may provide attraction more than a predetermined range between the first housing 10 and the cap portion 90 such that the first housing 10 and the cap portion 90 are easily separated by the external force of the user of the aerosol generation device 100, but are not separated by a general external force. The binding means may be, for example, a magnetic material, but is not limited thereto.

The cap portion 90 may accommodate the first housing 10 therein to prevent foreign substances from being inserted into the first housing 10 and to prevent breakage or damage of the first housing 10. When the cap portion 90 is coupled to the aerosol generation device 100, the outer surface of the cap portion 90 and the outer surface of the case 80 may be continuously connected to each other to form an appearance of the aerosol generation device 100. As a result, the aerosol generation device 100 may have an integral smooth appearance, thereby improving portability of the aerosol generation device 100.

The aerosol generation device 100 may further include the cover 30 mounted on one surface of the case 80 to cover the coupling portion 88 that couples the second housing 20 and the case 80. The cover 30 may cover the coupling portion 88 coupling the second housing 20 and the case 80 to prevent the coupling portion 88 from being exposed to the outside. Accordingly, the general access to the coupling portion 88 by the user of the aerosol generation device 100 may be prevented. Because the general access to the coupling portion 88 is prevented, arbitrary release or disassembly of the user of the aerosol generation device 100 may be prevented.

In addition, the aerosol generation device 100 may further include an adhesive portion 35 between one surface of the case 80 and the cover 30. An adhesive material may be applied to both surfaces of the adhesive portion 35 such that the cover 30 may be coupled to the case 80 through the adhesive portion 35.

When a component of the aerosol generation device 100 such as the cover 30 is coupled to the adhesive portion 35 and then separated from the adhesive portion 35, at least part of the adhesive portion 35 may be deformed to indicate that the cover 30 is separated from the case 80.

For example, when the user arbitrarily separates the cover 30 of the aerosol generation device 100 from the aerosol generation device 100, a predetermined mark may be remained on the adhesive portion 35 to indicate that the cover 30 is separated from the aerosol generation device 100.

Marking of the adhesive portion 35 may occur due to the deformation of at least part of the adhesive portion 35 when the cover 30 is separated. For example, when the cover 30 is separated, the adhesive material of the adhesive portion 35 is deformed, or a part or the whole of the adhesive portion 35 may be wrinkled or torn together with the adhesive material, which may cause the marking of the adhesive portion 35 to occur.

The mark remaining on the adhesive portion 35 is irreversible, and thus when the marking occurs on the adhesive portion 35, it is impossible to remove the mark from the adhesive portion 35. Therefore, information about the separation of the cover 30 of the aerosol generation device 100 may be provided through the adhesive portion 35.

Information about the separation of at least one of the first housing 10, the second housing 20, and the battery 110 of the aerosol generation device 100 may be provided through the information about the arbitrary separation of the cover 30 of the aerosol generation device 100.

The aerosol generation device 100 has a structure in which a fastening structure for fastening components of the aerosol generation device 100 is concealed, thereby preventing the fastening structure from being exposed to the outside and damaged by an external pressure or stimulation.

In addition, the aerosol generation device 100 may prevent breakage or damage of the aerosol generation device 100 that may occur when the user arbitrarily disassembles or releases the exposed fastening structure of the aerosol generation device 100.

An irreversible mark remains on the adhesive portion 35 that couples the cover 30 of the aerosol generation device 100 when the cover 30 is separated from the adhesive portion 35. After the mark remains on the adhesive portion 35, it is impossible to remove the mark from the adhesive portion 35 and thus, the information about the arbitrary separation of the cover 30 of the aerosol generation device 100 may be provided through the adhesive portion 35.

The information about the separation of at least one of the first housing 10, the second housing 20, and the battery 110 of the aerosol generation device 100 may be provided through the information about the arbitrary separation of the cover 30 of the aerosol generation device 100.

A method of assembling the aerosol generation device 100 according to exemplary embodiments may include providing the first housing 10 including the opening 11 in an upper portion, an inner space into which the cigarette 200 may be inserted through the opening 11, and the heater 130 positioned in the inner space; coupling the second housing 20 including the controller 120 to a lower portion of the first housing 10; coupling the first housing 10 and the second housing 20 through the fastening portion 50; coupling the battery 110 to the second housing 20, and coupling the case 80 to the second housing 20 to accommodate the second housing 20, the fastening portion 50, and the battery 110 therein.

As such, the fastening portion 50 may be prevented, by the case 80, from being exposed to the outside.

The configuration and effects of the method of assembling the aerosol generation device 100 according to exemplary embodiments are the same as those described above with respect to the aerosol generation device 100, and thus a redundant detailed description thereof will be omitted.

Those of ordinary skill in the art related to the embodiments may understand that various changes in form and details can be made therein without departing from the scope of the characteristics described above. The disclosed methods should be considered in descriptive sense only and not for purposes of limitation. The scope of the present disclosure is defined by the appended claims rather than by the foregoing description, and all differences within the scope of equivalents thereof should be construed as being included in the present disclosure.

What is claimed is:

1. An aerosol generation device comprising:
   a first housing comprising an opening opened at one side, an inner space accommodating a cigarette inserted through the opening, and a heater positioned in the inner space;
   a second housing comprising a controller and coupled to another side of the first housing;
   a fastening portion configured to couple the first housing and the second housing;
   a battery coupled to the second housing; and
   a case accommodating the second housing, the fastening portion, and the battery therein, and coupled to the second housing,
   wherein the fastening portion includes a first portion protruding from the other side of the first housing toward the second housing such that the first portion is located outside the second housing when the first housing is coupled to the second housing, and a second portion formed in the second housing,
   wherein the first housing and the second housing are coupled when the first portion and the second portion are coupled, and
   wherein the fastening portion is accommodated inside the case when the case is coupled to the second housing such that the fastening portion is covered by the case and the first housing is exposed to outside.

2. The aerosol generation device of claim 1, further comprising a switch electrically connected to the controller inside the second housing, wherein the case comprises a through hole exposing the switch to the outside.

3. The aerosol generation device of claim 1, further comprising a cap portion disposed outside the first housing to surround the first housing.

4. The aerosol generation device of claim 3, wherein an appearance of the aerosol generation device is formed by continuously connecting an outer surface of the cap portion and an outer surface of the case to each other.

5. The aerosol generation device of claim 1, further comprising:

a coupling portion configured to couple the second housing to the case; and a cover mounted on one surface of the case to cover the coupling portion.

6. The aerosol generation device of claim 5, further comprising an adhesive portion disposed between the case and the cover, wherein an adhesive material is applied to both sides of the adhesive portion.

7. The aerosol generation device of claim 6, wherein, when the cover coupled to the case by the adhesive portion is separated from the case, at least a part of the adhesive portion is deformed to indicate that the cover is separated from the case.

* * * * *